United States Patent [19]

Schulz et al.

[11] Patent Number: 4,478,758
[45] Date of Patent: Oct. 23, 1984

[54] PREPARATION OF SCHIFF BASES OF AMINOCYCLOALKANECARBOXYLIC ACIDS ESTERS

[75] Inventors: Günter Schulz; Ernst Buschmann; Bernd Zeeh, all of Ludwigshafen, Fed. Rep. of Germany

[73] Assignee: BASF Aktiengesellschaft, Fed. Rep. of Germany

[21] Appl. No.: 393,497

[22] Filed: Jun. 29, 1982

[30] Foreign Application Priority Data

Jul. 1, 1981 [DE] Fed. Rep. of Germany ....... 3125872

[51] Int. Cl.³ .................. C07C 121/78; C07C 119/14
[52] U.S. Cl. .............................. 260/465 D; 560/12; 560/18; 560/21; 560/35
[58] Field of Search ............... 260/465 D; 560/35, 12, 560/18, 21

[56] References Cited

U.S. PATENT DOCUMENTS 3,940,419  2/1976  Diehl et al. ............... 260/326 A
4,017,299  4/1977  Diehl et al. ............... 71/96
4,298,760  11/1981  Lee ............................ 562/506

FOREIGN PATENT DOCUMENTS 2824517 12/1979 Fed. Rep. of Germany .

OTHER PUBLICATIONS

D. H. Rich and J. P. Tam, Synthesis, (1978), p. 46.

U. Schöllkopf, D. Hoppe and R. Jentsch, Chem. Ber. 108, (1975), pp. 1580–1592.
I. Bregovec and T. Jakovcic, Monatsh. Chem. 103, (1972), pp. 288–291.
M. P. Periasamy and H. M. Walborsky, Organic Preparations and Procedures Int. 11 (6), (1979), pp. 293–311.
G. Stork, A. Y. W. Leong and A. M. Touzin, J. Org. Chem. 41, (1976), pp. 3491–3493.
B. Bey and J. P. Vevert, Tetrahedron Letters, (1977), pp. 1455–1458.

Primary Examiner—Dolph H. Torrence
Attorney, Agent, or Firm—Keil & Weinkauf

[57] ABSTRACT

Schiff bases of aminocycloalkanecarboxylic acid esters of the formula

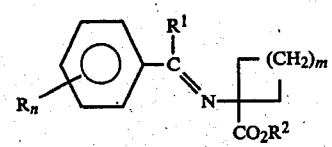

I where R, $R^1$, $R^2$, m and n have the meanings given in the description, are prepared by a novel process. The compounds are intermediates for the preparation of the corresponding aminocycloalkanecarboxylic acids and of esters thereof.

1 Claim, No Drawings

PREPARATION OF SCHIFF BASES OF AMINOCYCLOALKANECARBOXYLIC ACIDS ESTERS

The present invention relates to a novel process for the preparation of Schiff bases of aminocycloalkanecarboxylic acid esters. These compounds are intermediates for the preparation of aminocycloalkanecarboxylic acid esters and aminocycloalkanecarboxylic acids, many of which are known (cf. D. H. Rich and J. P. Tam, Synth. (1978), 46; U. Schöllkopf, D. Hoppe and R. Jentsch, Chem. Ber. 108 (1975), 1580; I. Bregovec and T. Jakovcié, Monatsh. Chem. 103 (1972), 288), and which are or can be converted into growth-regulating active ingredients (cf. German Laid-Open Application DOS 2,342,229).

German Laid-Open Application DOS 2,824,517 has disclosed that aminocycloalkanecarboxylic acids having a growth-regulating action are obtained when isocyanoacetic acid esters are cycloalkylated with $\alpha,\omega$-dihaloalkanes and the resulting isocyanocycloalkanecarboxylic acid esters are hydrolysed. However, this synthesis route has some disadvantages, in particular the unpleasant odor and the toxicity of the volatile compounds of the isonitrile type (M. P. Periasamy and H. M. Walborsky, Organic Preparations and Procedures Int. 11 (6) (1979), 293-311).

G. Stork, A. Y. W. Leong and A. M. Touzin, J. Org. Chem. 41, 3491, and U.S. Pat. No. 4,298,760 have also disclosed that the readily obtainable and easily manageable Schiff bases of glycine esters can be dialkylated with alkyl iodides, using very strong bases, eg. lithium diisopropylamide. However, the alkylation of anions of N-arylideneglycine esters with non-activated alkyl bromides or alkyl chlorides has so far been considered impossible (B. Bey and J. P. Vevert, Tetrahedron Lett. (1977), 1455-1458).

The present invention relates to a process for the preparation of Schiff bases of aminocycloalkanecarboxylic acid esters of the formula I

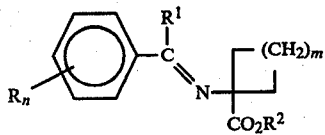

where R is hydrogen, halogen, alkyl, alkoxy, alkylthio, alkylsulfonyl, haloalkyl, nitro, cyano, unsubstituted or substituted phenyl or unsubstituted or substituted phenoxy, $R^1$ is hydrogen, alkyl, alkenyl, alkynyl, unsubstituted or substituted cycloalkylalkyl or unsubstituted or substituted aryl, $R^2$ is alkyl, alkenyl, alkynyl, unsubstituted or substituted cycloalkylalkyl, unsubstituted or substituted arylalkyl or unsubstituted or substituted aryl, n is 1, 2 or 3 and m is an integer from 0 to 8, and 1 or 2 hydrogen atoms in the cycloalkyl ring can be replaced by alkyl, alkenyl, alkynyl, unsubstituted or substituted cycloalkylalkyl, unsubstituted or substituted arylalkyl or unsubstituted or substituted aryl, wherein an aminoacetic acid derivative of the formula II

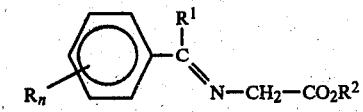

where R, $R^1$, $R^2$ and n have the above meanings, is reacted with an $\alpha,\omega$-disubstituted alkane of the formula III $$X-CH_2-(CH_2)_m-CH_2-Y \qquad (III)$$

where m has the above meanings, the alkylene group can be substituted as described above and X and Y independently of one another are each Cl, Br, I, O-tosyl or O-mesyl, in the presence of a base.

If, for example, N-benzylideneglycine ethyl ester and 1,2-dibromoethane are used as starting materials, the course of the reaction can be represented by the following equation:

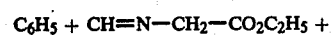

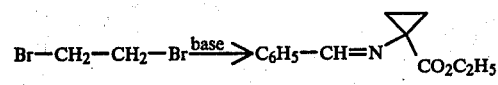

The reaction according to the invention is preferably carried out in the presence of a diluent, in particular a mixture of dimethylsulfoxide and ether, preferably in a ratio of from 1:2 to 1:3. Suitable bases are compounds of the formula MeR, where Me is an alkali metal, preferably sodium or potassium, and R is hydrogen or O-$C_2$-$C_5$-alkyl. Potassium tert.-butylate and sodium hydride are particularly preferred.

The reaction can be carried out at temperatures within a substantial range, generally at from 0° to 50° C., preferably from 20° to 35° C.

Preferably, 1 mole of the $\alpha,\omega$-disubstituted alkane III and from 2 to 2.2 moles of base are used per mole of glycine ester Schiff base II in the process according to the invention. The compounds of the formula I are isolated in a conventional manner.

In formula I, R is preferably hydrogen, fluorine, chlorine, bromine, nitro or cyano, or alkyl or alkylsulfonyl of 1 to 4 carbon atoms, or alkoxy or alkylthio of 1 to 2 carbon atoms, or haloalkyl of not more than 4 carbon atoms and not more than 5 halogen atoms, in particular of not more than 2 carbon atoms and not more than 3 identical or different halogen atoms, eg., preferably, fluorine and chlorine. A specific example of haloalkyl is trifluoromethyl. In addition, R is preferably unsubstituted phenyl or phenoxy, or phenyl or phenoxy which is monosubstituted or polysubstituted by identical or different substituents such as, preferably, halogen, in particular fluorine, chlorine and bromine, cyano and nitro, and haloalkyl of not more than 2 carbon atoms and not more than 3 identical or different halogen atoms, preferably fluorine and chlorine. A specific example of haloalkyl is trifluoromethyl.

$R^1$ and $R^2$ and the substituents on the cycloalkyl ring are each independently of one another preferably hydrogen (with the exception of $R^2$), or alkyl, alkenyl or alkynyl of not more than 4 carbon atoms, or cycloalkylalkyl where cycloalkyl is of 5 to 7 carbon atoms and is unsubstituted or substituted by alkyl of 1 to 4 carbon atoms, or benzyl (with the exception of $R^1$) which is unsubstituted or monosubstituted or polysubstituted by identical or different substituents, or phenyl which is unsubstituted or substituted by different substituents, preferred substituents on the benzyl and phenyl including halogen, in particular fluorine, chlorine and bromine, cyano, nitro, acetylamino, alkyl of not more than 4 carbon atoms, phenyl, phenoxy and haloalkyl of not more than 2 carbon atoms and not more than 3 identical or different halogen atoms, in particular flourine and chlorine. A specific example of haloalkyl is trifluoromethyl. n is preferably 1 or 2 and m is preferably a number from 0 to 6.

Specific compounds are shown in the Table below.

| $R_n$ | $R^1$ | ⌐(CH₂)ₘ<br>└─┘ | $R^2$ |
|---|---|---|---|
| H | H |  | $C_2H_5$ |
| 2-Cl | H |  | $C_2H_5$ |
| 4-Cl | H |  | $C_2H_5$ |
| 2,4-Cl₂ | H |  | $C_2H_5$ |
| 4-NO₂ | H |  | $C_2H_5$ |
| 2,4-(NO₂)₂ | H |  | $C_2H_5$ |
| 4-Phenoxy | H |  | $C_2H_5$ |
| 3-CF₃ | H |  | $C_2H_5$ |
| H | CH₃ |  | $C_2H_5$ |
| 2,4-Cl₂ | CH₃ |  | $C_2H_5$ |
| 3,4-Cl₂ | CH₃ |  | $C_2H_5$ |
| 2,5-Cl₂ | CH₃ |  | $C_2H_5$ |
| H | C₆H₅ |  | $C_2H_5$ |
| H | C₆H₅ |  | $C_2H_5$ |
| 4-Cl | 4-Cl—C₆H₅ |  | $C_2H_5$ |

-continued

| $R_n$ | $R^1$ | ⌐(CH₂)ₘ<br>└─┘ | $R^2$ |
|---|---|---|---|
| H | H |  | tert.C₄H₉ |
| H | H |  | $C_2H_5$ |
| H | H |  | $C_2H_5$ |
| H | H |  | $C_2H_5$ |
| H | H |  | $C_2H_5$ |
| H | H |  | $C_2H_5$ |
| H | H |  | $C_2H_5$ |
| H | H |  | $C_2H_5$ |
| H | H |  | $C_2H_5$ |
| H | H |  | $C_2H_5$ |
| H | H | 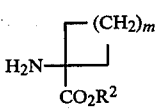 | $C_2H_5$ |

The compounds of the formula I are valuable intermediates for the preparation of aminocycloalkanecarboxylic acid esters of the formula IV $$H_2N-\underset{CO_2R^2}{\overset{\ulcorner(CH_2)_m}{\underset{\llcorner\quad\lrcorner}{\phantom{x}}}} \qquad \text{IV}$$

and aminocycloalkanecarboxylic acids of the formula V

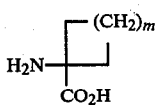

V where $R^2$, $R_3$ and m have the above meanings and the cycloalkyl ring can be substituted as described.

The compounds IV and V, some of which are known, are growth-regulating active ingredients. They can easily be prepared in an advantageous manner from the Schiff bases I.

The aminocycloalkanecarboxylic acid esters IV are obtained by hydrolyzing a Schiff base I with excess aqueous acid in the presence or absence of a solubilizing agent. After the aldehyde or ketone also obtained in the hydrolysis has been separated off from the aqueous phase, the aminoacid ester IV is liberated by addition of an acid acceptor and is isolated in a conventional manner.

Suitable acids include aqueous organic acids, eg. formic acid, acetic acid, oxalic acid and citric acid, and dilute aqueous mineral acids, eg. hydrochloric acid, sulfuric acid, nitric acid and phosphoric acid. Preferably, from 2 to 10 times the theoretically required amount of acid is used.

Suitable solubilizing agents include water-miscible organic solvents, which may be inert, such as nitriles, eg. acetonitrile, alcohols, eg. methanol, ethanol and propanol, and ethers, eg. tetrahydrofuran and dioxane.

Suitable acid acceptors include all the inorganic or organic acid acceptors which can usually be employed, preferably alkali metal carbonates, eg. sodium carbonate, sodium bicarbonate and potassium carbonate.

The reaction temperature can be varied within a substantial range, and is generally from 0° to 100° C., preferably from 20° to 30° C.

The compounds of the formula V are obtained by hydrolyzing a Schiff base I or an ester IV with an aqueous base in the presence or absence of a solubilizing agent. After any aldehyde or ketone also formed in the hydrolysis has been separated off from the aqueous phase and the product has been neutralized, the aminocycloalkanecarboxylic acid is isolated in a conventional manner.

Suitable aqueous bases include aqueous solutions of alkali metal or alkaline earth metal hydroxides, eg. potassium hydroxide, sodium hydroxide, calcium hydroxide and, preferably, barium hydroxide.

Preferred acids for the neutralization include aqueous mineral acids, eg. hydrochloric acid, sulfuric acid, nitric acid and phosphoric acid, sulfuric acid being particularly preferred. The compounds V can be isolated in a salt-free form in a simple manner by combining hydrolysis with barium hydroxide and neutralization with sulfuric acid, and separating off the barium sulfate.

Suitable solubilizing agents include water-miscible organic solvents, which may be inert, such as nitriles, eg. acetonitrile, alcohols, eg. methanol, ethanol and propanol, and ethers, eg. tetrahydrofuran and dioxane.

The reaction temperature can be varied within a substantial range, and is generally from 0° to 100° C., preferably from 50° to 100° C.

Some of the Schiff bases of the glycine esters of the formula II, used as the starting material, are known (cf. eg.: M. J. O'Donnell, J. M. Boniece and S. E. Earp, Tetrahedron Lett. (1978), 2641; P. Bey and J. P. Vevert, Tetrahedron Lett. (1977), 1455; O. Gerngross and A. Olcay, Chem. Ber. 96 (1963), 2550; G. Stork, A. Y. W. Leong and A. M. Touzin, J. Org. Chem. 41 (1976), 3491). Those which are not known can be obtained in a conventional manner from an aminoacid ester and a corresponding ketone or aldehyde by condensation with elimination of water (cf. Methoden der Organischen Chemie (Houben-Weyl), E. Müller, Editor, Volume, XV, 1, Chapter 31, page 230 or "The Chemistry of the Carbon Nitrogen Double Bond", S. Patai, Editor, Interscience, New York 1970).

Examples of the Schiff bases II are:

| $R_n$ | $R^1$ | $R^2$ |
|---|---|---|
| H | H | $C_2H_5$ |
| 2-Cl | H | $C_2H_5$ |
| 4-Cl | H | $C_2H_5$ |
| 2,4-$Cl_2$ | H | $C_2H_5$ |
| 4-$NO_2$ | H | $C_2H_5$ |
| 2,4-$(NO_2)_2$ | H | $C_2H_5$ |
| 4-Phenoxy | H | $C_2H_5$ |
| 3-$CF_3$ | H | $C_2H_5$ |
| H | $CH_3$ | $C_2H_5$ |
| 2,4-$Cl_2$ | $CH_3$ | $C_2H_5$ |
| 3,4-$Cl_2$ | $CH_3$ | $C_2H_5$ |
| H | $C_6H_5$ | $C_2H_5$ |
| 4-Cl | 4-Cl-$C_6H_4$ | $C_2H_5$ |
| H | H | tert.-$C_4H_9$ |

The α,ω-disubstituted alkanes of the formula III also to be used as starting materials are generally known compounds or organic chemistry. Preferred compounds of the formula III are those where X and Y independently of one another are each Cl, Br or O-tosyl, eg. 1,2-dibromoethane, 1,2-dichloroethane, 1,2-dichloropropane, 1,3-dibromopropane, 1,4-dibromobutane, 3,4-dichlorobutane, 1,3-dichlorobutane, 2,3-dichlorobutane, 1,5-dibromopentane, 1,6-dibromohexane, 1,7-dibromoheptane, 1,8-dibromooctane.

The preparation examples illustrate the preparation of the novel intermediates of the formula I and their use.

PREPARATION EXAMPLES

EXAMPLE 1

Ethyl N-benzylidene-1-amino-cyclopropanecarboxylate 25.2 g (1.05 moles) of sodium hydride are added a little at a time under nitrogen to 100 g (0.523 mole) of N-benzylideneglycine ethyl ester and 45.1 ml (0.523 mole) of 1,2-dibromoethane in 500 ml of dry diethyl ether and 170 ml of dry dimethylsulfoxide, so that the well-stirred mixture remains at from 20° to 30° C. The mixture is stirred at room temperature overnight and filtered, and 1 l of water is added to the filtrate. The ethereal phase is separated off, washed with twice 200 ml of water, dried over sodium sulfate and evaporated under reduced pressure to give 80 g (70%) of ethyl N-benzylidene-1-aminocyclopropanecarboxylate as an oil.

$^1$H-NMR ($CDCl_3$): δ=1.2–1.9, m [4]; 1.28 t, J=7 Hz. [3]; 4.23, q, J=7 Hz [2]; 7.25–7.95, m [5]; and 8.40, s [1] broadened.

The compound can be converted into the aminocyclopentanecarboxylic acid of melting point 229°–231° C. by hydrolysis.

EXAMPLE 2

Ethyl N-benzylidene-1-aminocyclopropanecarboxylate 260 g (2.3 moles) of potassium tert.-butylate are added a little at a time to 200 g (1.05 moles) of N-benzylideneglycine ethyl ester and 90.5 ml (1.05 moles) of 1,2-dibromoethane in 900 ml of dry diethyl ether and 300 l of dry dimethylsulfoxide, so that the well-stirred mixture remains at from 25° to 35° C. The mixture is stirred at room temperature overnight and excess base is then neutralized by addition of 4N hydrochloric acid. The mixture is diluted with 1.5 l of water and the ethereal phase is separated off, washed with twice 300 ml of water, dried with sodium sulfate and evaporated to give 155 g (68%) of ethyl N-benzylidene-1-aminocyclopropanecarboxylate as an oil.

The $^1$H-NMR spectrum corresponds to that of the substance in Example 1.

EXAMPLE 3

Ethyl N-benzylidene-1-aminocyclopentanecarboxylate 117 g (91%) of ethyl N-benzylidene-1-aminocyclopentanecarboxylate are obtained as an oil by a method similar to that in Example 2, starting from 100 g (0.523 mole) of N-benzylideneglycine ethyl ester and 62.1 ml (0.523 mole) of 1,4-dibromobutane in 450 ml of ether and 150 ml of dimethylsulfoxide, using 130 g (1.15 moles) of potassium tert.-butylate as the base. Characteristic $^1$H-NMR signals (CDCl$_3$): $\delta = 1.6$–$2.5$, m [8]; and 8.20, s [1] broadened.

The compound can be converted into the aminocyclopentanecarboxylic acid of melting point 320°–322° C. (decomposition) by hydrolysis.

EXAMPLE 4

Ethyl N-benzylidene-1-aminocycloheptanecarboxylate 258 g (90%) of ethyl N-benzylidene-1-aminocycloheptanecarboxylate are obtained as an oil by a method similar to that in Example 2, starting from 200 g (1.05 moles) of N-benzylideneglycine ethyl ester and 170 ml (1.05 moles) of 1,6-dibromohexane.

Characteristic $^1$H-NMR signals (CDCl$_3$): $\delta = 1.0$–$2.3$, m [12+3]; and 8.27, s [1] broadened.

The compound can be converted into the aminocycloheptanecarboxylic acid of melting point 350° C. (decomposition) by hydrolysis.

EXAMPLE 5

Ethyl N-benzylidene-1-aminocyclooctanecarboxylate 138 g (92%) of ethyl N-benzylidene-1-aminocyclooctanecarboxylate are obtained as an oil by a method similar to that in Example 1, starting from 100 g (0.523 mole) of N-benzylideneglycine ethyl ester and 89.9 ml (0.523 mole) of 1,7-dibromoheptane.

Characteristic $^1$H-NMR signals (CDCl$_3$): $\delta = 0.9$–$2.2$, m[14+3]; and 8.27, s [1] broadened.

The compound can be converted into the aminocyclooctanecarboxylic acid of melting point 310°–316° C. (decomposition) by hydrolysis.

We claim:

1. A process for the preparation of a Schiff base of an aminocycloalkanecarboxylic acid ester of the formula I

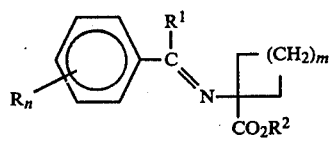

where R is hydrogen, halogen, alkyl, alkoxy, alkylthio, alkylsulfonyl, haloalkyl, nitro, cyano, unsubstituted phenyl, unsubstituted phenoxy or a phenyl or phenoxy hich is substituted with the same or different substituents selected from the group consisting of cyano, nitro, halogen and haloalkyl of not more than 2 carbon atoms, $R^1$ is hydrogen, alkyl, alkenyl, alkynyl, an unsubstituted cycloalkyl of from 5 to 7 carbon atoms or a cycloalkyl substituted with an alkyl of from 1 to 4 carbon atoms, unsubstituted aryl or aryl substituted by the same or different substituents selected from the group consisting of halogen, cyano, nitro, acetylamino, an alkyl of not more than 4 carbon atoms, phenyl, phenoxy and a haloalkyl of not more than 2 carbon atoms, $R^2$ is alkyl, alkenyl, alkynyl, an unsubstituted cycloalkyl of from 5 to 7 carbon atoms or a cycloalkyl substituted with an alkyl of from 1 to 4 carbon atoms, unsubstituted aryl, unsubstituted arylalkyl or an aryl or arylalkyl which is substituted by the same or different substituents selected from the group consisting of halogen, cyano, nitro, acetylamino, an alkyl of not more than 4 carbon atoms, phenyl, phenoxy and haloalkyl of not more than 2 carbon atoms, n is 1, 2 or 3 and m is an integer of from 0 to 8, and 1 or 2 hydrogen atoms in the cycloalkyl ring can be replaced by alkyl, alkenyl, alkynyl, a cycloalkyl of from 5 to 7 carbon atoms or a cycloalkyl substituted with an alkyl of from 1 to 4 carbon atoms, aryl, arylalkyl or an aryl or arylalkyl which is substituted by the same or different substituents selected from the group consisting of halogen, cyano, nitro, acetylamino, alkyl of not more than 4 carbon atoms, phenyl, phenoxy and a haloalkyl of not more than 2 carbon atoms, wherein an aminoacetic acid derivative of the formula II

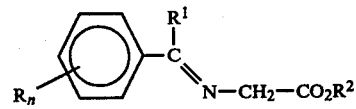

where R, $R^1$, $R^2$ and n have the above meanings, is reacted with an $\alpha,\omega$-disubstituted alkane of the formula III

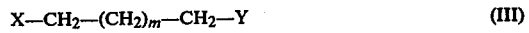

where m has the above meanings, the alkylene group can be substituted as described above and X and Y independently of one another are each Cl, Br, I, O-tosyl or O-mesyl, in the presence of an alkali tertiary butylate and a diluent consisting essentially of dimethylsulfoxide and ether.

* * * * *